(12) United States Patent
Kato

(10) Patent No.: US 7,834,773 B2
(45) Date of Patent: Nov. 16, 2010

(54) SMOKE DETECTOR

(75) Inventor: Kenichi Kato, Tokyo (JP)

(73) Assignee: Nohmi Bosai Ltd., Tokyo (JP)

( * ) Notice: Subject to any disclaimer, the term of this patent is extended or adjusted under 35 U.S.C. 154(b) by 318 days.

(21) Appl. No.: 12/073,318

(22) Filed: Mar. 4, 2008

(65) Prior Publication Data

US 2008/0218365 A1 Sep. 11, 2008

(30) Foreign Application Priority Data

Mar. 8, 2007 (JP) .............................. 2007-058496

(51) Int. Cl.
*G08B 17/00* (2006.01)
(52) U.S. Cl. ...................... 340/630; 340/628; 340/693.6
(58) Field of Classification Search ................. 340/630, 340/628, 629, 632, 633, 634, 693.6
See application file for complete search history.

(56) References Cited

U.S. PATENT DOCUMENTS 4,857,895 A * 8/1989 Kaprelian .................... 340/630
5,598,147 A * 1/1997 Mochizuki et al. .......... 340/630
5,610,592 A * 3/1997 Okazaki ...................... 340/628
6,285,291 B1 * 9/2001 Knox et al. .................. 340/634
6,288,647 B1 * 9/2001 Yamano ...................... 340/630

* cited by examiner

*Primary Examiner*—Toan N Pham
(74) *Attorney, Agent, or Firm*—Wenderoth, Lind & Ponack, L.L.P.

(57) ABSTRACT

A smoke detector having a structure in which, at a time of performing smoke detection, an S/N ratio of a signal of a light receiving element is improved, to thereby accurately detect the occurrence of a fire. At opposite end portions of an inside of an optical case (21) having a substantially cylindrical shape, a light emitting element (11) and a stray light portion (22) are arranged. In the stray light portion (22), a light trap (23) is provided. Further, in the vicinity of the light emitting element (11), a condenser lens (24) is provided to allow light L to be incident on a curved surface of the light trap (23). At the time of smoke detection, light scattered by smoke particles in a smoke detection portion (25) is received by a light receiving element (12). However, the light that is incident on the light trap (23) is reflected on the curved surface a plurality of times to be attenuated in each reflection, so the light is not received by the light receiving element (12). Accordingly, the S/N ratio of an output signal S obtained from the light receiving element (12) is improved, thereby making it possible to accurately perform smoke detection at an early stage.

8 Claims, 11 Drawing Sheets

SMOKE DETECTOR

BACKGROUND OF THE INVENTION

1. Field of the Invention

The present invention relates to a smoke detector for optically detecting contaminants such as smoke floating in the air.

2. Description of the Related Art

A smoke detector is used for preventing fire or as a detecting system at a time of occurrence of fire or in a semiconductor manufacturing plant or a food industry requiring a certain level of environmental conservation.

Conventionally, there are suggested various smoke detectors. In the following, as an example thereof, an outline of a "smoke detecting apparatus" disclosed in JP 11-23460 A will be described.

That is, the smoke detecting apparatus for determining fire by optically detecting smoke particles floating in the air sucked from a monitor space includes a laser diode which emits a laser beam having an electric field component in a predetermined direction, and an image formation lens for forming a light source image of an emission surface of the laser diode in a smoke detection region through which the sucked air passes. The smoke detecting apparatus also includes a light receiving element disposed on an optical axis that passes through an image forming position of the light source image in the smoke detection region, and is set on a surface substantially parallel to a direction of the electric field component of the laser beam, for receiving scattered light of the smoke particles, which has passed through the image forming position of the light source image and the vicinity thereof.

With this structure, in a case where there are suspended matters such as smoke particles in the air, the laser beam impinges upon the smoke particles to be scattered and the scattered light is received by the light receiving element. As a result, it is possible to sense generation of the smoke.

However, according to study of the inventor of the present invention, new problem is revealed regarding the detection of the smoke.

That is, generation of the smoke is detected by receiving the scattered light in a smoke detection portion by the light receiving element. However, when light other than the scattered light diffuses in an optical case, the diffused light is also received by the light receiving element. When an output signal of the light receiving element corresponding to the scattered light is represented by reference symbol S and an output signal thereof corresponding to the diffused light is represented by reference symbol N, an output in which the output signal S which is an original sensed signal is added with the output signal N which is a noise component is obtained.

In order to perform the smoke detection with high sensitivity, it is necessary that a level difference between the output signals S and N be made larger to increase an S/N ratio. In order to achieve this, intensity of light passing through the smoke detection portion has to be increased and diffusion of stray light has to be reduced.

On the other hand, the smoke detector is installed as a disaster prevention system in a building, a plant, or the like, so it is preferable that the smoke detector be small and light.

SUMMARY OF THE INVENTION

The present invention has been made in view of the above-mentioned problems. It is an object of the present invention to provide a smoke detector in which an S/N ratio at the time of smoke detection is high and which has a simple structure and can be reduced in size and weight. It is another object of the present invention to provide a smoke detector of a suction type, in which fine particles other than smoke particles entering inside a smoke detection portion do not remain in a field range of the light receiving element.

According to a first aspect of the present invention, there is provided a smoke detector including: an optical case formed in a substantially cylindrical shape; an air passage which constitutes a smoke detection portion by allowing a gas to flow into the optical case; a light emitting element disposed in the optical case; a light receiving element for receiving scattered light generated by scattering light emitted from the light emitting element by smoke particles existing in the smoke detection portion; a light trap opposed to the light emitting element, for attenuating stray light; a condenser lens for condensing the light emitted from the light emitting element in the vicinity of the light trap; a received light amplifier circuit for amplifying an output signal of the light receiving element; and a fire determination portion for determining fire when a detection level obtained by A/D-converting the amplified output signal is equal to or larger than a threshold value, in which the light trap has a curved surface which reflects the stray light a plurality of times and attenuates the stray light.

According to a second aspect of the present invention, there is provided a smoke detector including: an optical case having, in a black box: a light emitting element; a light receiving element having a predetermined optical axis angle with respect to the light emitting element, for receiving scattered light of the light emitting element scattered by smoke particles in a smoke detection portion; and an optical trap opposed to the light emitting element, for attenuating stray light; and an air passage for sampling, which passes across the smoke detection portion of the optical case, in which, of an inner wall surface in the smoke detection portion of the optical case, a portion in a field range of the light receiving element is formed to be a smooth surface and a portion outside the field range is formed to be an irregular surface.

According to a third aspect of the present invention, there is provided a smoke detector including: an optical case having an inner portion constituting a black box; a first air passage which constitutes a smoke detection portion by allowing a gas, which is to be detected, to flow into the optical case; a second air passage for allowing a clean gas to flow through a peripheral portion of the first air passage; a light emitting element disposed in the optical case; a light receiving element for receiving scattered light generated by scattering light emitted from the light emitting element by smoke particles existing in the smoke detection portion; a light trap opposed to the light emitting element, for attenuating stray light; a received light amplifier circuit for amplifying an output signal of the light receiving element; and a fire determination portion for determining fire when a detection level obtained by A/D-converting the amplified output signal is equal to or larger than a threshold value.

The first aspect of the present invention includes the above-mentioned structure, thereby exerting various effects as described below.

That is, the light emitted from the light emitting element is condensed in the vicinity of the light trap by the condenser lens so as to pass through the smoke detection portion into which smoke to be sensed flows with air. When the smoke is generated in the gas, the light is scattered by the smoke particles. The scattered light is received by the light receiving element, and an output signal S which is a sensed signal is obtained from the light receiving element.

In this case, the light passing through the smoke detection portion is incident on the optical trap. The optical trap has a curved surface, so the incident light impinges upon the curved surface to be reflected a plurality of times, to thereby be attenuated. Therefore, the light is scattered and is not received by the light receiving element. An output signal N which is a noise component is hardly generated, thereby making it possible to perform smoke detection excellent in S/N ratio with high sensitivity.

Further, a shape of the light trap is simple, so the optical case can be downsized, by extension, the smoke detector as a whole can be reduced in size and weight.

The second aspect of the present invention includes the above-mentioned structure. Accordingly, of a beam applied from the light emitting element, light which impinges upon the smooth surface in the field range of the light receiving element is reflected outside the field range and the reflected light impinges upon the irregular surface outside the field range, to thereby be attenuated. As a result, reception of noise light (diffracted light) by the light receiving portion is substantially eliminated, thereby enabling accurate fire detection.

The third aspect of the present invention includes the above-mentioned structure, thereby exerting the various effects as described below.

That is, the light emitted from the light emitting element is condensed in the vicinity of the light trap by the condenser lens so as to be transmitted through the smoke detection portion into which the smoke to be sensed flows with air. The smoke detection portion allows passage of a sampling air obtained through the first filter and passage of clean air in a manner that the clean air surrounds an outer periphery of the sampling air, the clean air being obtained by further filtering the sampling air by the second filter or being obtained through another system.

At the time of fire detection, a laser beam is allowed to pass through the smoke detection portion. However, the clean air functions as a so-called air curtain with respect to the sampling air. Accordingly, scattering of the sampling air including the smoke particles is inhibited, and at the same time, mixing of dust or the like other than the smoke particles can be inhibited. In a case where fire occurs, the laser beam impinges upon the smoke particles to be scattered, and the scattered light is received by the light receiving element, to thereby detect the fire. A suspended matter other than the smoke particles is not mixed into the sampling air in the optical case, so the fire detection can be performed accurately and with high sensitivity, thereby enhancing reliability of the smoke detector.

DETAILED DESCRIPTION OF THE PREFERRED EMBODIMENTS

As a result of research and experiments by the inventor of the present invention for solving the above-mentioned problems, the following were found. In order to improve an S/N ratio, light emitted from a light emitting element is condensed on a curved surface portion of a light trap by a condenser lens. On the other hand, the light trap has a curved surface structure which reflects the incident light a plurality of times.

As a result, luminance of scattered light generated by smoke particles at a time of smoke detection increases, thereby making a level of an output signal S obtained from a light receiving element higher. The light incident on the light trap is attenuated during the plurality of times of reflection and is not received by the light receiving element. Accordingly, a level of an output signal N which is a noise component is lowered, and the S/N ratio is improved, thereby making it possible to perform the smoke detection with high sensitivity.

Embodiment 1

Hereinafter, a first embodiment of the present invention will be described in detail with reference to FIGS. 1 to 4.

Figure 1:
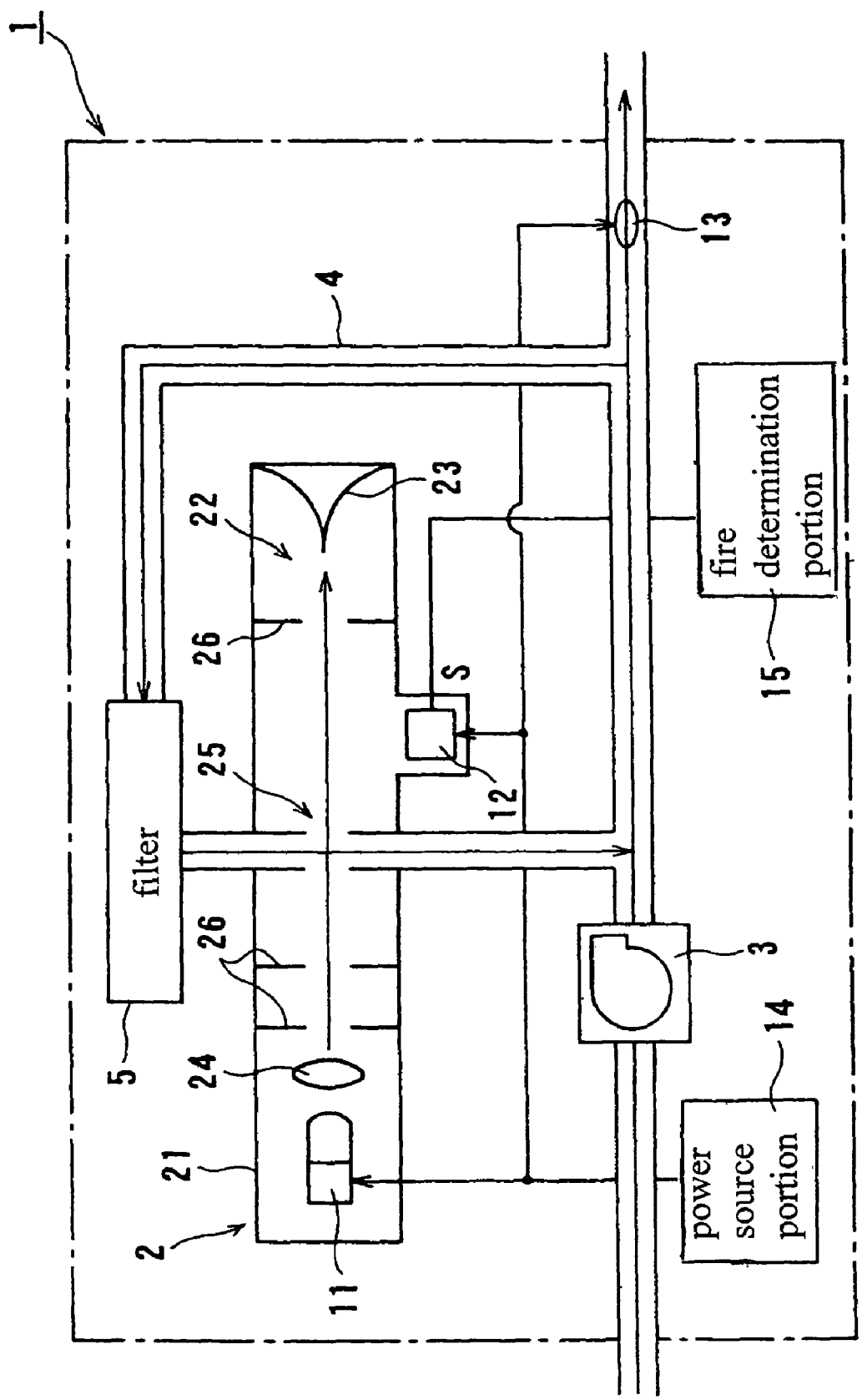
FIG. 1 is a structural diagram showing a smoke detector according to a first embodiment of the present invention.

A description is made of an entire structure of a smoke detector 1 with reference to FIG. 1. The smoke detector 1 includes a smoke detection unit 2, a fan 3 for sending air to be sensed by the smoke detection unit 2, a piping 4 serving as an air passage, a filter 5, a light emitting element 11 disposed in the smoke detection unit 2, a light receiving element 12 such as a photodiode, a power source portion 14 for supplying power to the fan 3 and an air flow sensor 13 for measuring a flow rate of air, a fire determination portion 15, and the like.

Note that the fire determination portion 15 includes an amplifier circuit for amplifying an output signal S of the light receiving element 12, an A/D converter for converting an amplified signal to a detection level, a comparator circuit for determining fire when the detection level becomes equal to or larger than a preset threshold value, and the like. Integrated control is performed by a CPU.

Next, a description will be made of the smoke detection unit 2 with reference to FIG. 2. In an optical case 21 configured in a substantially cylindrical shape, there are arranged, for example, the light emitting element 11 emitting an infrared ray and a stray light portion 22 positioned at a position opposed to the light emitting element 11. Between those, there are provided a condenser lens 24 for condensing the emitted light on a curved surface portion of a light trap 23 provided in the stray light portion 22, a smoke detection portion 25 for allowing passage of air, the light receiving element 12, and the like. Note that, apertures 26 are provided at predetermined intervals to limit irradiation light.

Figure 3:
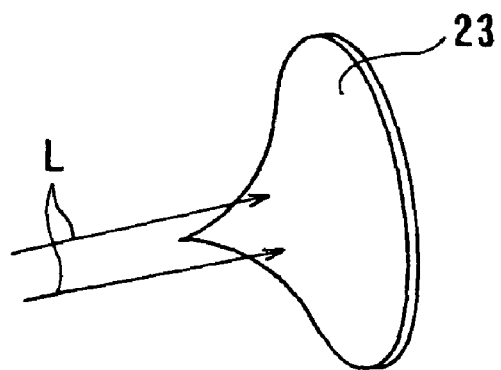
FIG. 3 is a perspective view of a light trap.
Figure 4:
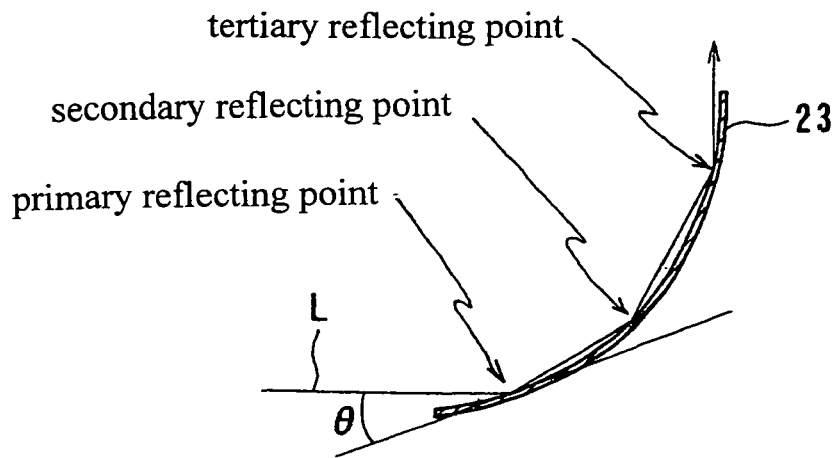
FIG. 4 is a sectional view showing a reflection mode of light on the light trap.

The light trap 23 according to this embodiment is formed in a substantially conical shape as shown in FIG. 3. Light L entering the stray light portion 22 is incident on a curved surface of the light trap 23 to be reflected a plurality of times as shown in FIG. 4. A reflected light amount of the light L is reduced in each reflection at the curved surface so that the light L is not diffused as diffused light to the smoke detection portion 25 side, in other words, to a field range of the light receiving element 12.

According to study of the inventor of the present invention, the curved surface may be of a coaxial circular shape or an elliptical shape. By the way, the more acute an incident angle $\theta$ of the light L with respect to a tangent line of the curved surface is, the higher the effect becomes. Through simulation, such an analysis was made that, when the incident angle $\theta$ is equal to or smaller than 45°, a plurality of times of reflection are performed, and especially, when the incident angle $\theta$ is equal to or smaller than 30°, as shown in FIG. 4, three times or more reflection are performed.

Accordingly, the curved surface is not limited to the shape shown in FIG. 4. When the curved surface is formed in an elliptical shape, a larger number of reflection are obtained.

In the following, a description will be made of a smoke detection operation according to this embodiment.

Figure 2:
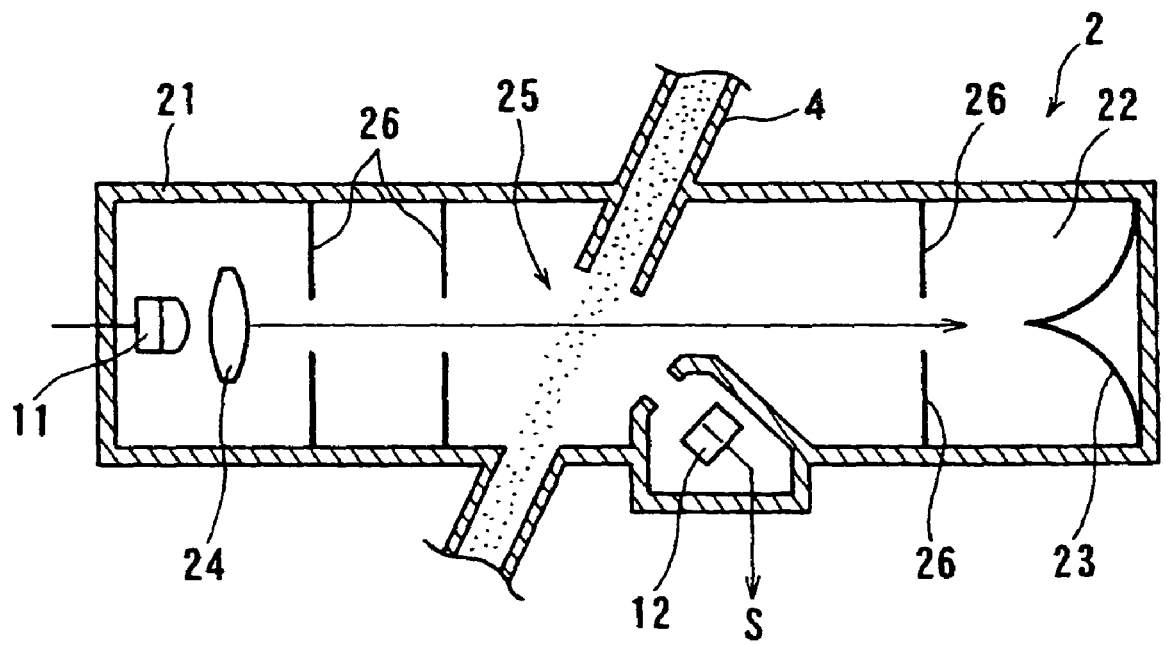
FIG. 2 is a sectional view showing a structure of a smoke detection unit.

In a normal state, air sucked from a monitor space by the fan 3 flows from a top to a bottom of the smoke detection portion 25 shown in FIG. 2. When the air is clean, the light L is not scattered in the smoke detection portion 25, and the light L enter the inside of the stray light portion 22 while being condensed and in a state where a focal point is adjusted on the curved surface of the light trap 23.

On the light trap 23, a plurality of times of reflection are performed as shown in FIG. 4. The light L is attenuated in accordance with the number of times of the reflection. Accordingly, the stray light is not received by the light receiving element 12 and the output signal S is at a low level, so the determination on fire is not made.

At the time of occurrence of fire, smoke particles float in the sucked air. When the smoke particles are irradiated with the light L, the scattered light is generated in the smoke detection portion 25. The scattered light is received by the light receiving element 12. The output signal S corresponding to a received light amount is derived. The output signal S is supplied to the fire determination portion 15 and a processing of the signal is performed to notify the occurrence of fire by display or sound.

The light L which has passed through the smoke detection portion 25 is reflected as described above by the light trap 23, so the light L is attenuated, thereby not being received as the stray light. Accordingly, even at the time of occurrence of fire, the S/N ratio of the output signal is high, and the fire determination is correctly performed with high sensitivity and high accuracy.

Figure 5:
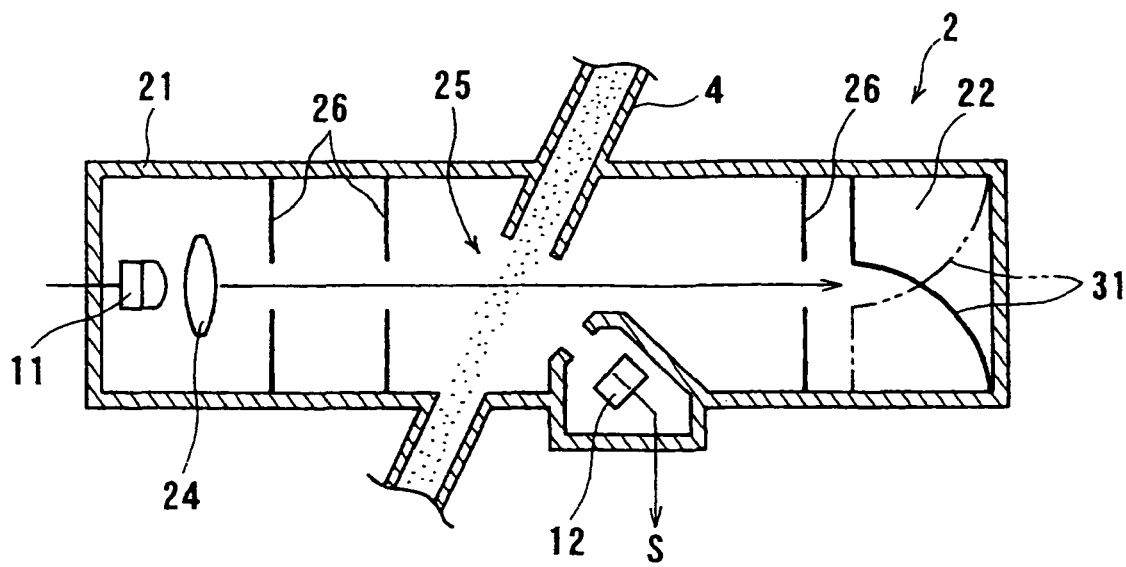
FIG. 5 is a sectional view showing a smoke detection unit according to a second embodiment of the present invention.

Next, with reference to FIG. 5, a description will be made of a second embodiment of the present invention. Note that a difference between this embodiment and the first embodiment is that the shape of the light trap is changed. Accordingly, the same components as that of the first embodiment are denoted by the same reference symbols and the repetitive description is avoided.

In this embodiment, as a light trap 31, a plate-like body formed with a curved surface was applied.

With this structure, the light L is reflected a plurality of times as shown in the figure, thereby making it possible to reduce the stray light. Accordingly, as described above, the output signal S which is excellent in S/N ratio is derived from the light receiving element 12, thereby making it possible to accurately perform the fire detection without failure in operation.

Note that in this embodiment, an inclination direction of the light trap 31 is not limited to the direction shown by a solid line and may be changed to a direction shown by a chain double-dashed line. Accordingly, a degree of design freedom is enhanced.

Further, in both the first and second embodiments, condensation is performed by the condenser lens 24 disposed at a large distance from the light trap 23, 31. Accordingly, adjustment of the focal point at the incident position with respect to the light trap 23, 31 and the incident angle can be made uniform, thereby making it possible to accurately achieve a plurality of times of reflection. Accordingly, the stray light is reliably attenuated, thereby making it possible to improve the S/N ratio.

Further, the light trap 23, 31 can be moved on an optical axis. Accordingly, even when there is individual variation in the condenser lens 24 or the light emitting element, the focal point can be easily adjusted. Further, the structure can be simplified, thereby enabling downsizing of the smoke detection unit 2.

Figure 6:
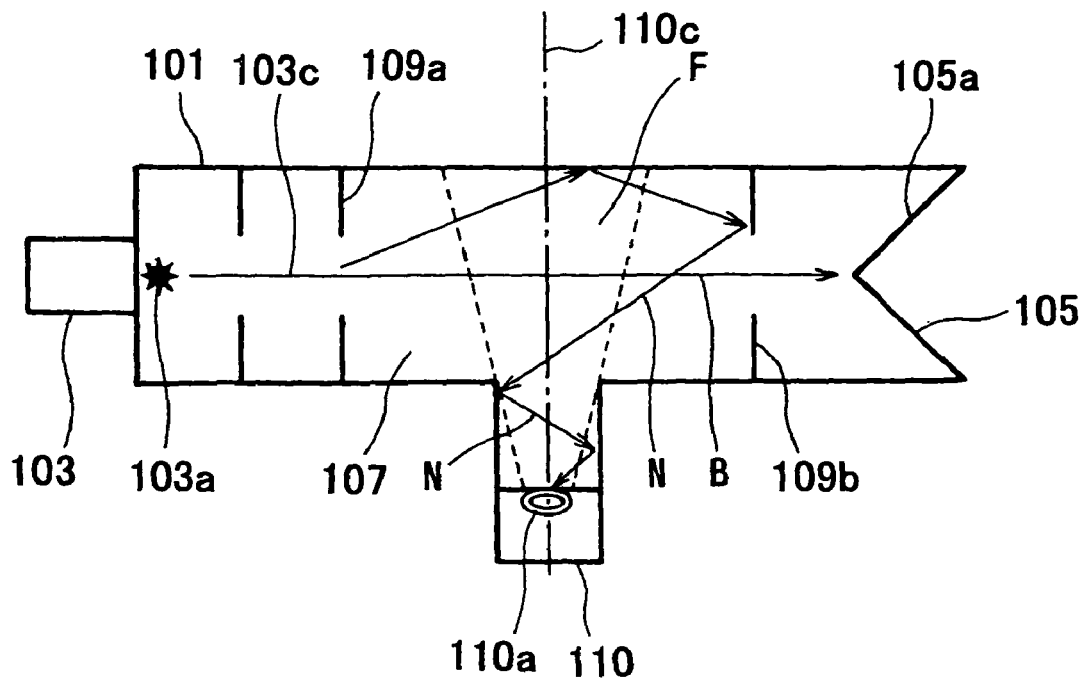
FIG. 6 is a vertical sectional view showing a third embodiment of the present invention.
Figure 7:
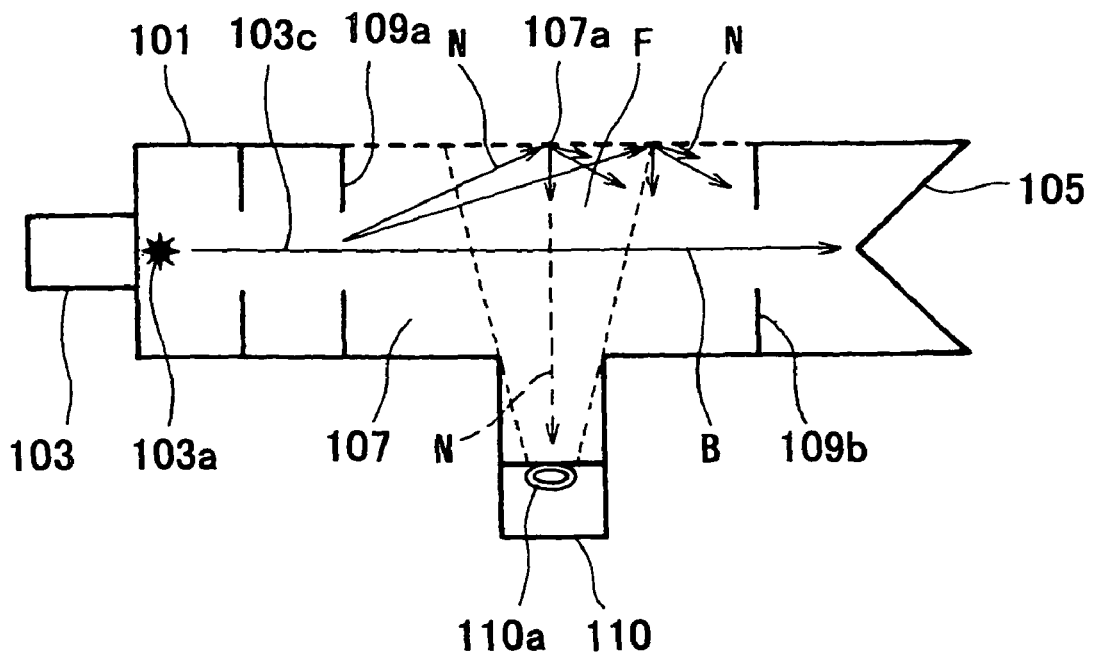
FIG. 7 is a vertical sectional view showing a fourth embodiment of the present invention.
Figure 8:
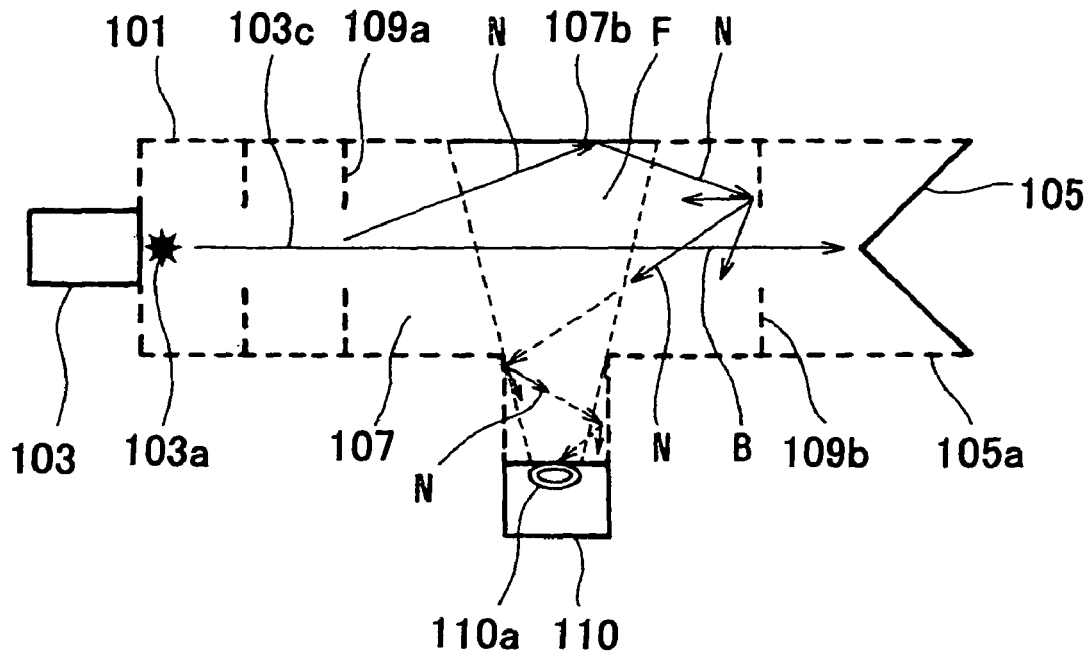
FIG. 8 is a vertical sectional view showing a fifth embodiment of the present invention.

The inventor of the present invention thought that the noise light is received by the light receiving portion by being affected by a level of smoothness of a wall surface of the smoke detection portion. In this case, studies were made on a case where, as shown in FIG. 6, an entire inner wall surface of the smoke detection portion is a smooth surface (third embodiment), a case where, as shown in FIG. 7, only an entire part of the inner wall surface of the smoke detection portion, which is opposed to the light receiving portion, is an irregular surface (fourth embodiment), and a case where, as shown in FIG. 8, of the wall surface of the smoke detection portion, a part in the field range of the light receiving portion is a flat surface and the other portion is an irregular surface (fifth embodiment). The smooth surface may be not only a glossy mirror surface but also one having a smooth surface causing regular reflection of the incident light. On the other hand, the irregular surface may be one having a rough surface causing diffuse reflection of the incident light. Hereinafter, a description will be made of each of the embodiments.

Smoke Detector of Third Embodiment

An optical case 101 of a substantially cylindrical shape has one end provided with a light emitting portion 103 and another end provided with a stray light portion 105. The light emitting portion 103 is provided with a light emitting element 103a including the condenser lens, and the stray light portion 105 is provided with a light trap 105a for attenuating the stray light.

In the optical case 101, a smoke detection portion 107 is provided. Both end portions of the smoke detection portion 107 is defined by apertures 109a and 109b. On a side wall of the smoke detection portion 107, there are provided an air passage (not shown) for sampling, which passes across the smoke detection portion 107, a light receiving portion 110 which receives scattered light, and a light shielding plate (not shown) for preventing light of the light emitting element 103a from directly entering the light receiving portion 110.

The light receiving portion 110 includes a light receiving element 110a. An optical axis 110c of the light receiving element 110a is orthogonal with an optical axis 103c (main beam) of the light emitting element 103a. An entire inner wall surface of the smoke detection portion 107 is formed with a surface without irregularities, that is, a so-called smooth surface.

Next, a description will be made of an operation of the smoke detector.

Light applied from the light emitting element 103a passes through a through hole of the aperture 109a, enters the smoke detection portion 107, and straightly travels in the smoke detection portion 107. The light which straightly travels passes through the aperture 109b, reaches the stray light portion 105, and is then attenuated by the light trap 105a.

In this case, while the light is converged by the through hole of the aperture 109a to be a main beam B, a diffracted light (noise light) N is generated in the vicinity of the through hole.

The diffracted light N impinges upon the inner wall surface in a field range (monitoring range) F of the light receiving portion 110 to be reflected. The reflected light N impinges upon the aperture 109b positioned outside the field range F to be reflected. The reflected light N impinges upon the inner wall surface in the vicinity of an inlet of the light receiving portion 110 to be reflected. The reflected light N further impinges upon the inner wall surface of the light receiving portion 110 and is then received by the light receiving element 110a. Note that a part of the diffracted light N impinges upon the inner wall surface outside the field range F to be reflected, and the reflected light directly enters the light receiving portion 110 in some cases.

In this way, the diffracted light (noise light) N impinges upon the inner wall surface and repeats the plurality of times of reflection to reach the light receiving portion 110. However, the inner wall surface is the smooth surface at which the incident angle and the reflection angle are substantially equal to each other, so the noise light cannot be attenuated to a sufficient degree.

Smoke Detector of Fourth Embodiment

In FIG. 7, the same reference symbols as those of FIG. 6 denote components which have the same names and functions as those of FIG. 6.

A difference between a smoke detector of this embodiment and the smoke detector of the case 101 is that, of the inner wall surface of the smoke detection portion 107, a portion opposed to the light receiving portion 110 (portion inside field range F and portion in the vicinity of field range F) is formed to be the irregular surface and the other portion is formed to be the smooth surface.

In the smoke detector of this embodiment, the diffracted light N impinges upon the inner wall surface 107a in the field range (monitoring range) F of the light receiving portion 110 to be reflected. The reflected light N impinges upon the aperture 109b positioned outside the field range F to be reflected. In this case, the inner wall surface 107a is the irregular surface, so while a light absorbance thereof is high and a total sum of reflected energy is small, the reflected light is diffused. Accordingly, a part N1 of the diffused noise light directly reaches the light receiving portion 110. Therefore, the diffracted light N cannot be sufficiently attenuated.

Smoke Detector of Fifth Embodiment

In FIG. 8, the same reference symbols as those of FIG. 6 denote components which have the same names and functions as those of FIG. 6.

A difference between a smoke detector of this embodiment and the smoke detector of the case 101 is that, of the inner wall surface of the smoke detection portion 107, an inner wall surface 107b in the field range F of the light receiving portion 110 is formed to be the smooth surface and the other portion is formed to be the irregular surface.

In the smoke detector of this embodiment, the diffracted light N impinges upon the inner wall surface 107b in the field range (monitoring range) F of the light receiving portion 110 to be reflected. The reflected light N impinges upon the aperture 109b positioned outside the field range F to be reflected. In this case, the aperture 109b is the irregular surface, so the light absorbance thereof is high and the total sum of reflected energy is small. Further, the diffracted light N is repeatedly reflected while being subjected to light absorption by the irregular surface, thereby being greatly attenuated.

Note that, a part of the diffracted light generated in the vicinity of the through hole of the aperture 109a also impinges upon a portion other than the inner wall surface 107b of the field range F, that is, the inner wall surface outside the field range of the light receiving portion 110. In this case, the portion is the irregular surface. Accordingly, the light is efficiently absorbed and even when the noise light is diffused, the noise light is sufficiently attenuated until it reaches the light receiving portion 110.

As described above, as compared to the third and fourth embodiments, in the fifth embodiment, the attenuation of the diffracted light is great and an amount of the received light entering the light receiving portion is small, so accurate detection of fire or the like is enabled.

The present invention has been made based on the above-mentioned observation, and is characterized in that, of the inner wall surface in the smoke detection portion of the optical case, the portion in the field range of the light receiving element is formed to be the smooth surface and the portion outside the field range is formed to be the irregular surface.

Embodiment 2

Figure 9:
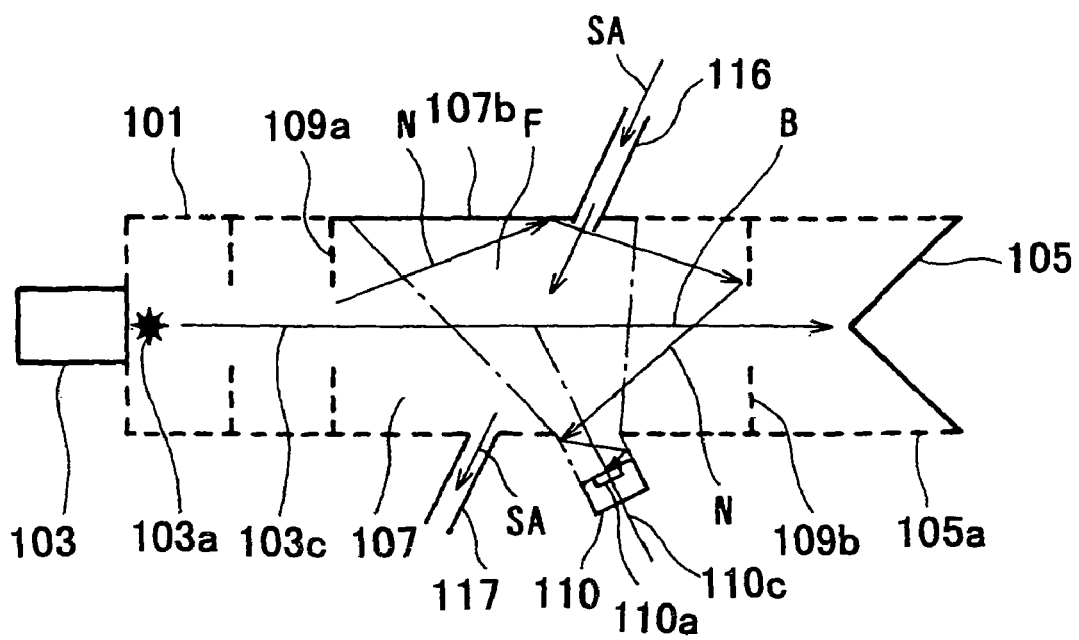
FIG. 9 is a vertical sectional view showing a sixth embodiment of the present invention.
Figure 10:
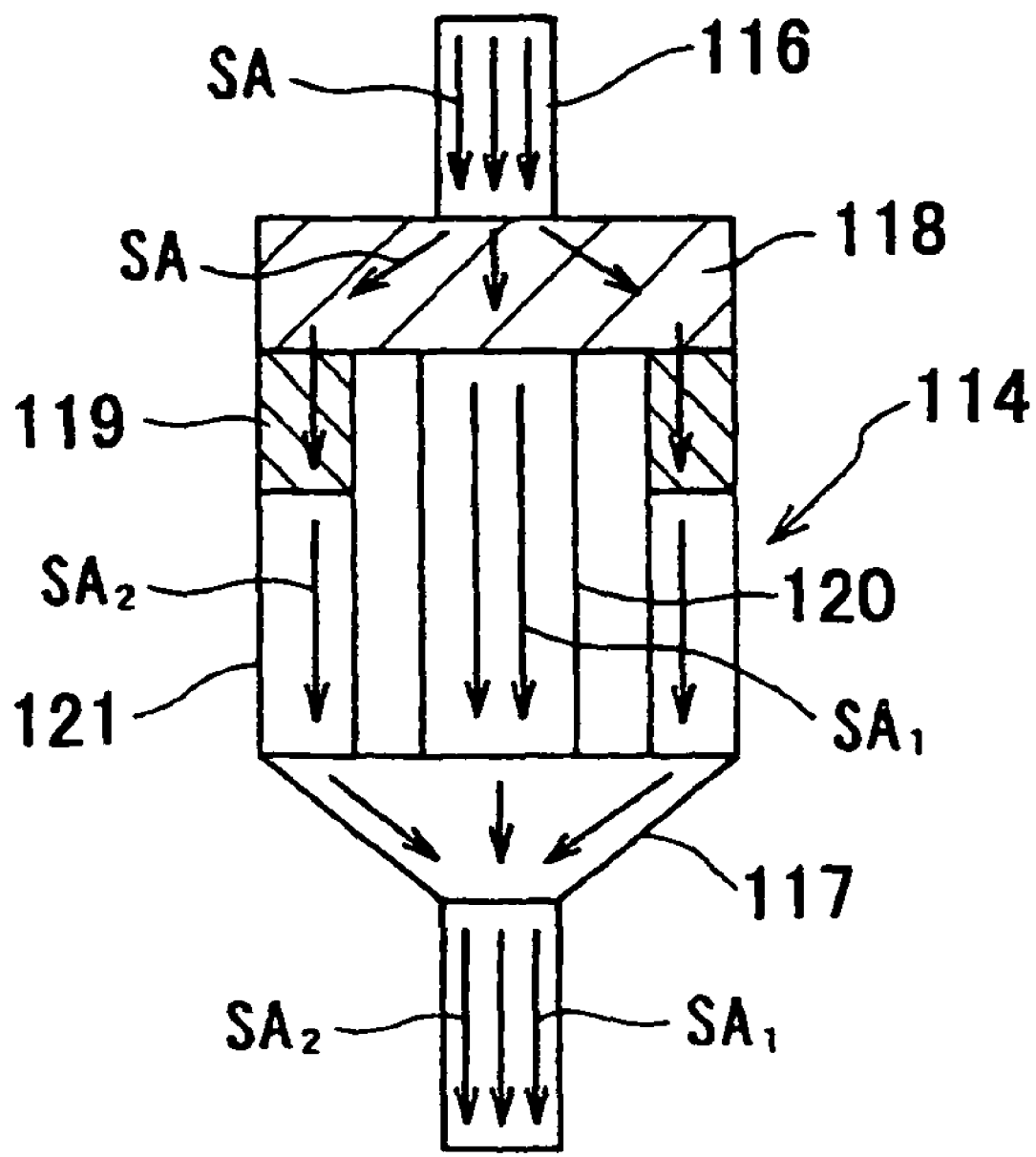
FIG. 10 is an enlarged view showing an air passage.
Figure 11:
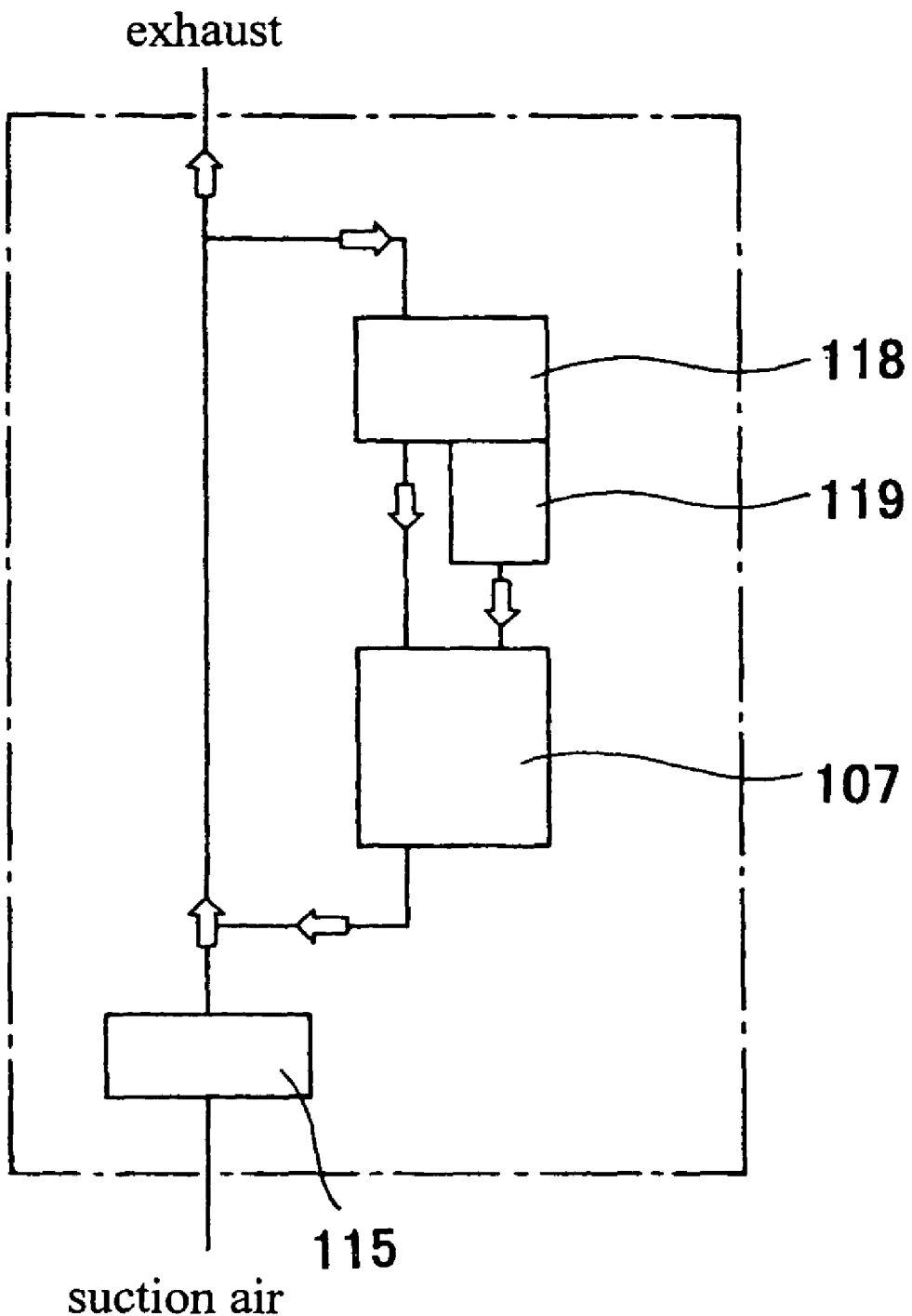
FIG. 11 is a structural diagram showing a flow path for suction and exhaustion of sampling air.

A sixth embodiment of the present invention will be described with reference to FIGS. 9 to 11.

The optical case 101 of the substantially cylindrical shape has the one end provided with the light emitting portion 103 and the other end portion provided with the stray light portion 105. The light emitting portion 103 is provided with the light emitting element 103a including the condenser lens. The stray light portion 105 is provided with the light trap 105a for attenuating the stray light.

In the optical case 101, there is provided the smoke detection portion 107. The both end portions of the smoke detection portion 107 are defined by the apertures 109a and 109b. On the side wall of the smoke detection portion 107, there are provided an air passage 114 for sampling, which crosses over the smoke detection portion 107, the light receiving portion 110 for receiving the scattered light, and the light shielding plate (not shown) for preventing light of the light emitting element 103a from directly entering the light receiving portion 110.

The air passage 114 for sampling is provided with a sampling pipe 116 for sucking a sampling air SA into the smoke detection portion by rotation of a fan 115, and an exhaust pipe 117 opposed to the sampling pipe 116 at an interval of the passage.

A distal end of the sampling pipe 116 is provided with a rough filter 118. On an outer peripheral portion of the rough filter 118, a fine filter 119 of a cylindrical shape having finer mesh is provided upright. Between the fine filter 119 and the exhaust pipe 117, there is formed a cleaning air passage (second air passage) 121 surrounding the sampling passage (first air passage) 120.

The light receiving portion 110 includes the light receiving element 110a. The optical axis 110c of the light receiving element 110a intersects with the optical axis 103c (main beam) of the light emitting element 103a at a predetermined angle.

Of the inner wall surface of the smoke detection portion 107, the inner wall surface 107b in the field range (monitoring range) F of the light receiving portion 110 is formed to be the smooth surface and the other portion is formed to be the irregular surface.

Next, an operation of this embodiment will be described.

When the fan 115 is rotated, the sampling air SA is sucked from the sampling pipe 116 into the smoke detection portion 107. The sucked sampling air SA passes through the rough filter 118 to allow large foreign matters such as rubbish to be eliminated, thereby becoming a sampling air SA1.

The sampling air SA1 passes through the sampling air passage (first air passage) 120 to be sucked in the exhaust pipe 117. A part of the sampling air SA1 passes through the fine filter 119 to be filtered, thereby being a clean air SA2. The clean air SA2 passes through the clean air passage 121 and travels while surrounding the sampling air SA1 to be sucked in the exhaust pipe 117.

The light applied from the light emitting element 103a of the light emitting portion 103 passes through the through hole of the aperture 109a to enter the smoke detection portion 107, straightly travels in the smoke detection portion 107, and then passes through the aperture 109b to reach the stray light portion 105 to be attenuated by the light trap 105a.

When smoke particles exist in the sampling air SA1 introduced from the air passage 114 when the light (main beam) passes through the smoke detection portion 107, the scattered light is generated, and the scattered light is to be received by the light receiving portion 110. When the scattered light is received by the light receiving portion 110, the output signal of the light receiving element 110a is amplified by the light receiving amplifier circuit (not shown) and is then subjected to A/D conversion to be output to the fire determination portion. When the output level is equal to or higher than the threshold value, the fire determination portion determines that there is the fire and issues a warning or the like.

When the light of the light emitting element 103a passes through the aperture 109a, the diffracted light (noise light) N is generated. The diffracted light N impinges upon the inner wall surface 107b in the field range (monitoring range) F of the light receiving portion 110 to be reflected. The reflected light N impinges upon the aperture 109b positioned outside the field range F to be reflected. In this case, the aperture 109b is the irregular surface, so the light absorbance is high and the total sum of the reflected energy is small. Further, the diffracted light N repeats reflection while being subjected to light absorption by the irregular surface, thereby being greatly attenuated.

Note that a part of the diffracted light N generated in the vicinity of the through hole of the aperture 109a also impinges upon the portion other than the inner wall surface 107b of the field range F, that is, the inner wall surface outside the field range of the light receiving portion 110. However, the portion is the irregular surface, so the light is efficiently absorbed and even when the noise light is diffused, the noise light is sufficiently attenuated until it reaches the light receiving portion 110.

Next, a description will be made of a smoke detection portion 206 according to a seventh embodiment of the present invention.

The smoke detection portion 206 allows passage of not only merely the air to be detected (sampling air) a, that is, a gas including smoke at the time of fire, but also passage of the sampling air a through a central portion and passage of clean air surrounding the sampling air a in an annular manner.

Figure 13:
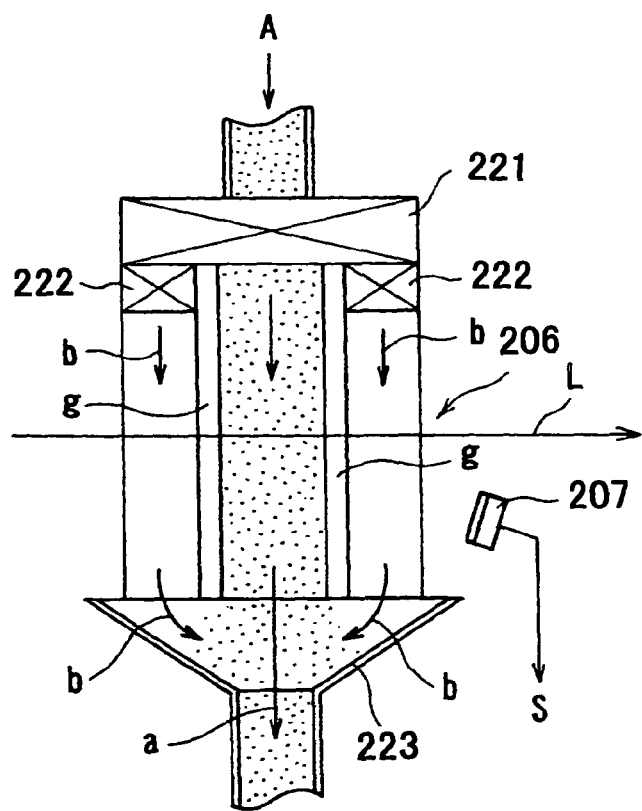
FIG. 13 is a sectional view showing a structure of a filter.

This structure is described in more detail. An air A sucked from the monitor space as shown in FIG. 13 is supplied to the first filter 221, and a part of the air roughly filtered is allowed to flow through the smoke detection portion 206 as the sampling air a. Further, a part of the air filtered by the first filter 221 is supplied to the second filter 222 to perform double-filtration, thereby obtaining an air b which is relatively clean with respect to the sampling air a. The clean air b is allowed to flow through a periphery of the sampling air a in the annular manner. Note that as the first and second filters 221 and 222, an HEPA filter or the like may be applied.

A structure of the first and second filters 221 and 222 may be a structure in which the second filter 222 formed in the annular shape is laminated to the first filter 221 formed in a disk-like shape as shown in FIG. 13. Between the outer surface of the first filter 221 and the inner surface of the second filter 222, a gap G of the annular shape is formed.

Figure 14:
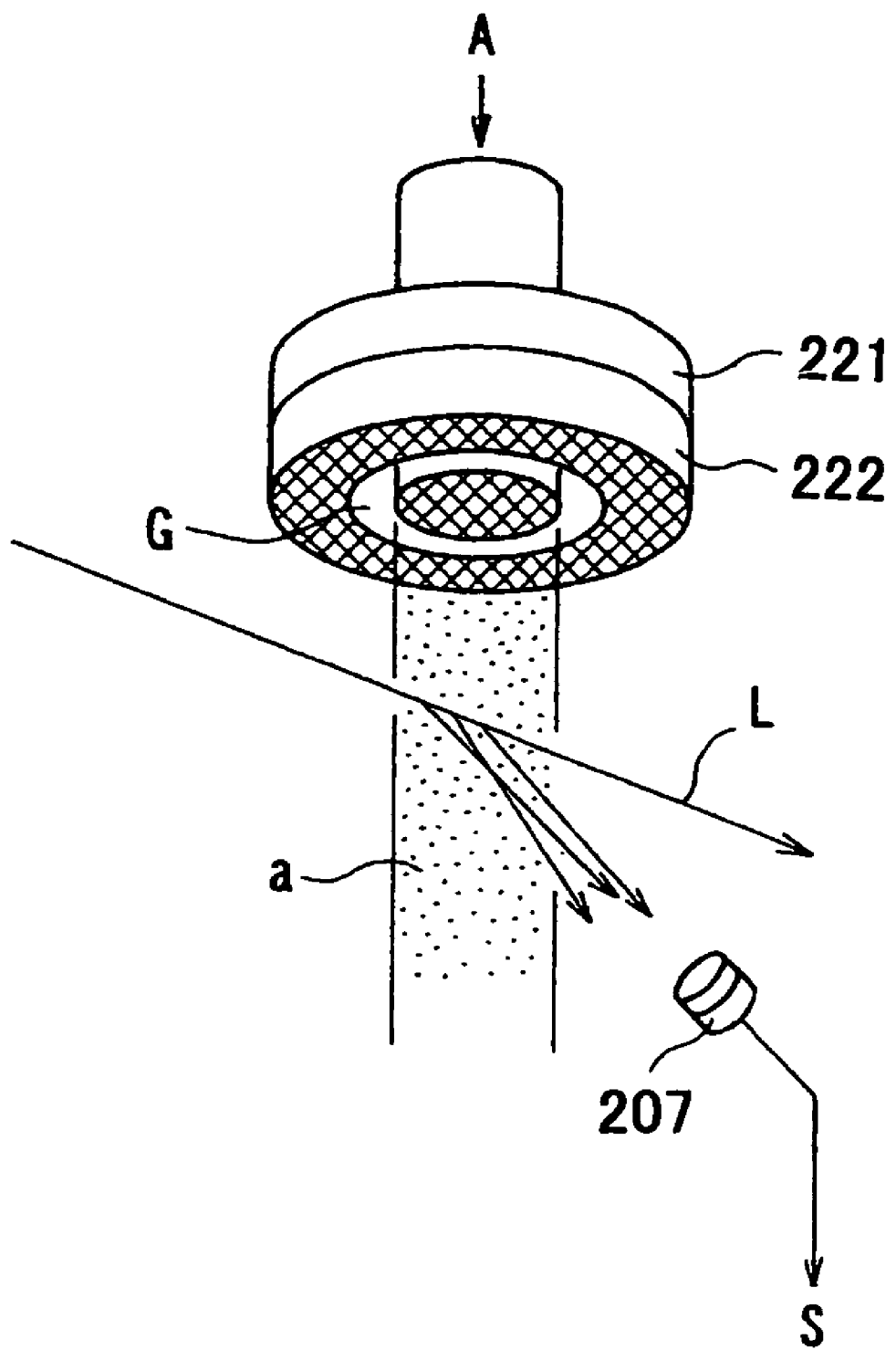
FIG. 14 is a perspective view showing the structure of the filter.

With this structure, between the sampling air a and the clean air b obtained through the double-filtration in the smoke detection portion 206, there is formed a gap g of an annular shape as shown in FIG. 14. While the sampling air a is roughly filtered, the clean air b is obtained through the double-filtration. Accordingly, a difference in flow rate is caused therebetween. That is, in this embodiment, with respect to the flow rate of the sampling air a, the flow rate of the clean air b is reduced. Accordingly, the clean air b does not disturb the flow of the sampling air a.

Note that after passing through the smoke detection portion 206, both the sampling air a and the clean air b are sucked from a suction portion 223 outside an optical case 202.

Figure 15:
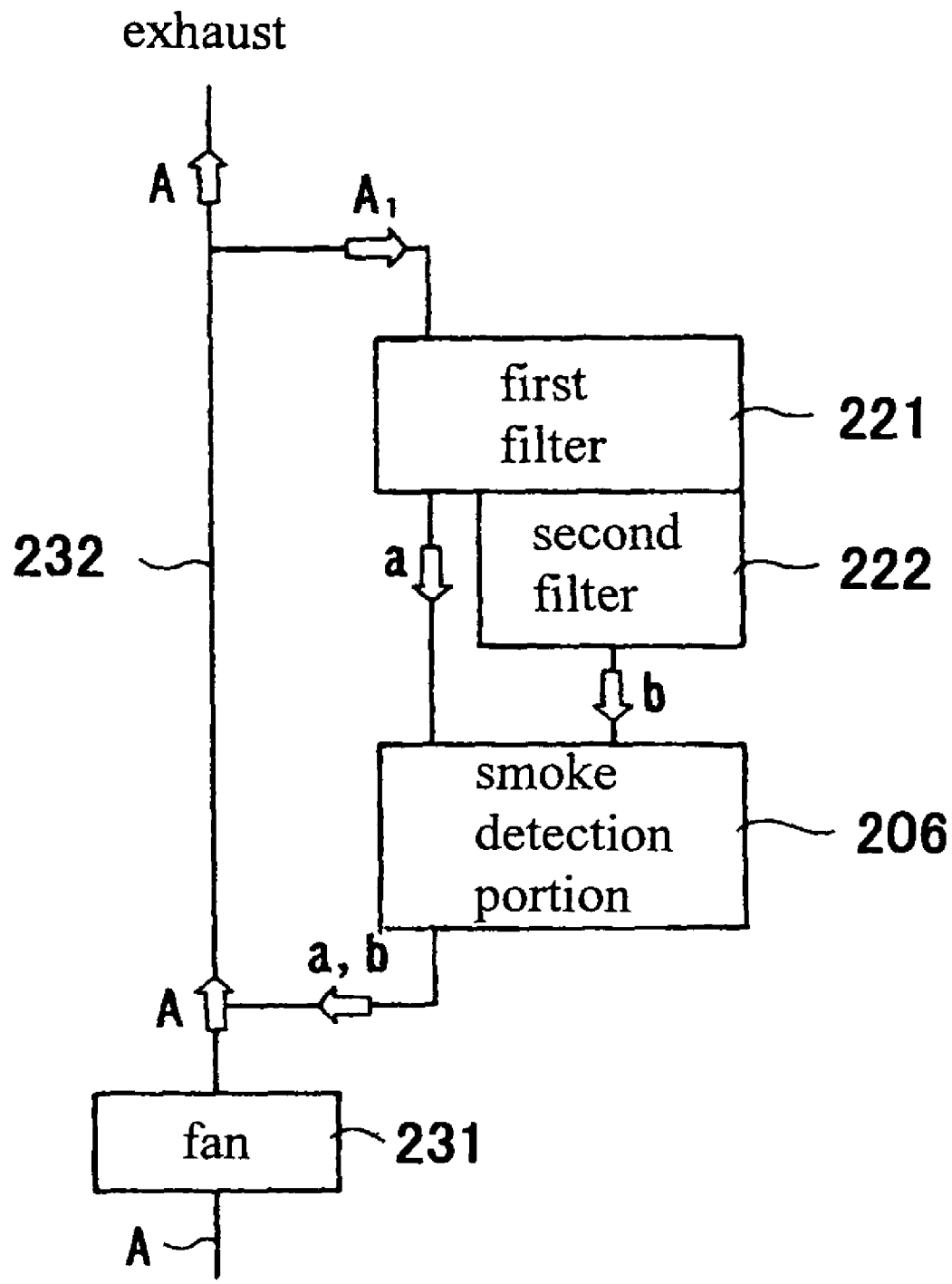
FIG. 15 is a system diagram showing flow of air.

Herein, circulation of the air A in the fire monitor space will be described. As shown in FIG. 15, the air A is sucked by a fan 231 and is sent to an exhaust side through a piping 232. A part thereof is sucked to the first filter 221 side as shown in an arrow A1. The air A is filtered by the first filter 221 thereby obtaining the sampling air a. At the same time, the clean air b is obtained from the second filter 222 to be supplied to the smoke detection portion 206 as described above.

Figure 12:
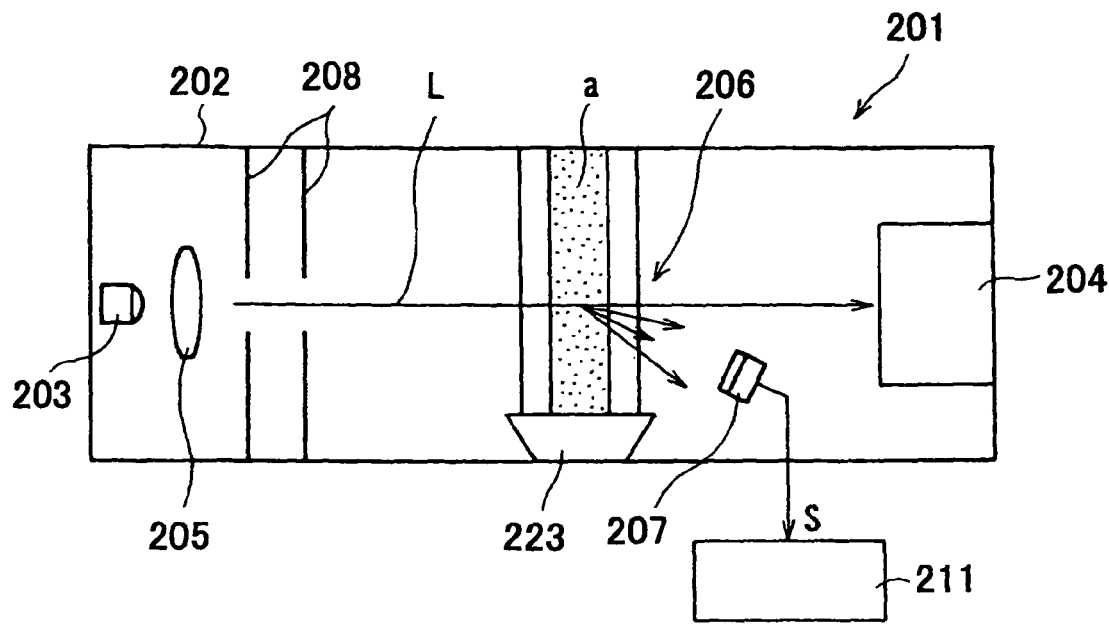
FIG. 12 is a structural diagram showing a smoke detector according to a seventh embodiment of the present invention.

In the case of performing smoke detection, as shown by an arrow L in FIGS. 12 to 14, passage of light emitted from a light emitting element 203, for example, a laser beam L is allowed. In the normal state, the sampling air a does not include therein smoke particles, so the laser beam L is not scattered in the smoke detection portion 206. Accordingly, an output signal S is not obtained from a light receiving element 207 and a fire determination portion 211 does not perform fire notification.

On the other hand, in a case where fire occurs in a fire monitoring area, the sampling air a includes therein smoke particles. In this case, the laser beam L impinges upon the smoke particles to be scattered and a part of the scattered light is received by a light receiving element 207. Accordingly, the output signal S is obtained from the light receiving element 207 and the fire determination portion 211 operates to notify occurrence of the fire.

When the fire determination portion 211 detects rise in smoke concentration in the optical case 202, in the case where a supply amount of the sampling air a is increased, the detection level quickly reaches a level equal to or larger than a threshold value. On the other hand, when the fire determination portion 211 detects dirt in the optical case 202, by stopping supply of the sampling air a to increase a supply amount of the clan air b, it is possible to blow away dust or the like remaining in the optical case 202. This is controlled by the fire determination portion 211.

The seventh embodiment exerts various effects as described below.

The clean air b functions as an air curtain with respect to the sampling air a, so the sampling air a is not scattered and the fire detection is accurately performed.

Further, the dirt in the optical case 202 can be reduced.

Further, even when the dust or the like adhering to a wall surface in the optical case 202 floats in the air, the dust or the like is not mixed into the sampling air a, making it possible to improve the S/N ratio of the fire detection.

Figure 16:
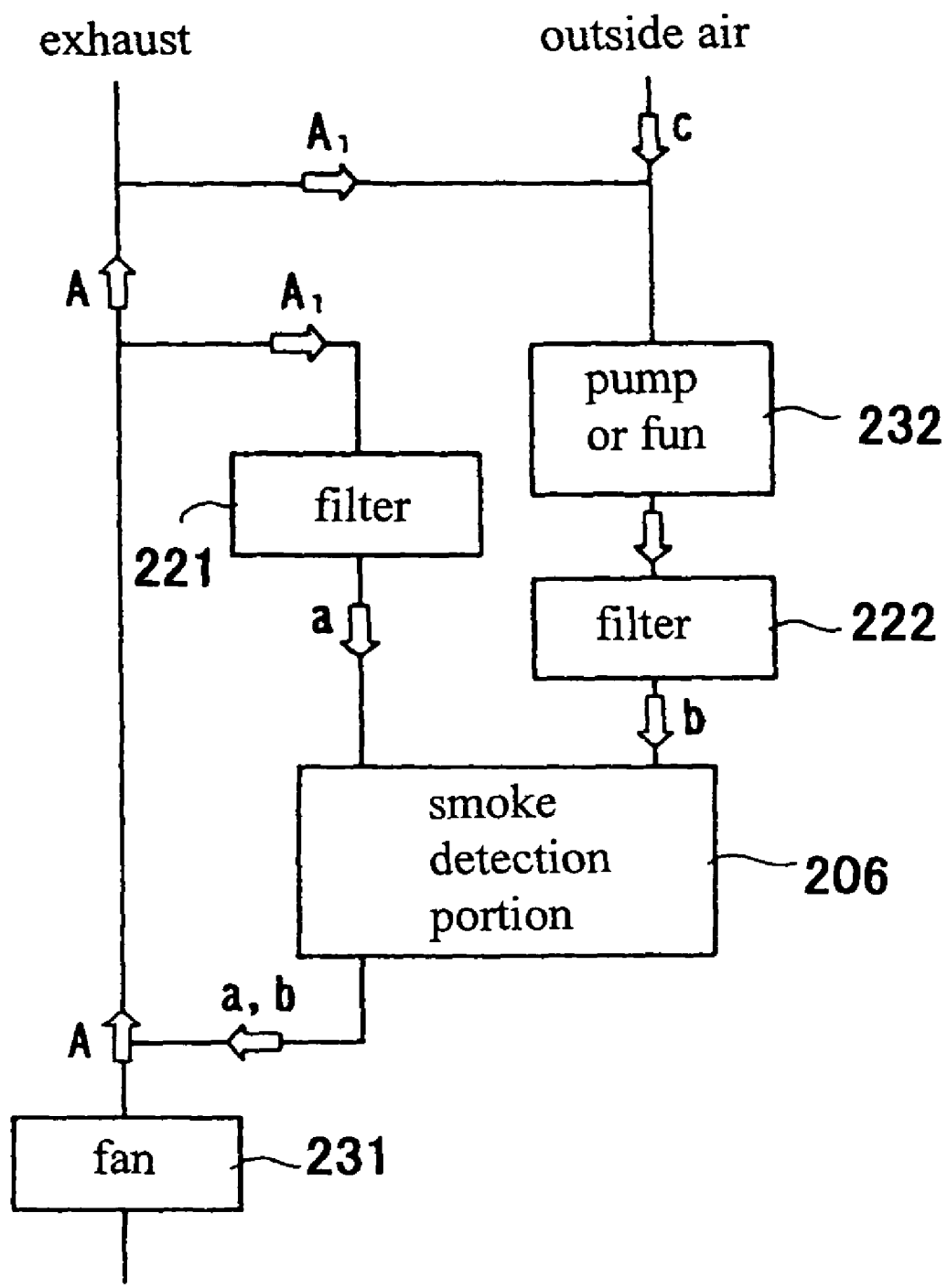
FIG. 16 is a system diagram showing an eighth embodiment of the present invention.

Next, with reference to FIG. 16, a description will be made of an eighth embodiment of the present invention.

This embodiment is structured such that the clean air b is obtained through a system different from that of the sampling air a.

That is, the part A1 of the air A in the monitoring area exhausted to a secondary side of the fan 231 and another outside air C are sucked and mixed with each other by a pump or a fan 232 to be supplied to the second filter 222. Further, the clean air b may be supplied from only one of the part A1 of the air A in the monitoring area and the outside air C.

The clean air b obtained from the second filter 222 is exhausted to an outer periphery of the sampling air a in the optical case 202 in the same manner as described above.

Even with this structure, occurrence of fire can be reliably sensed in the same manner as described above, an effect of preventing dirt or the like in the optical case 202 is obtained.

Further, with respect to the flow rate of the sampling air a, the flow rate of the clean air b can be freely changed, so multiple uses are possible, for example, the flow rate is temporarily increased to achieve a cleaning mode and the dust remaining in the optical case 202 is blown away. Also in this case, prevention of the diffusion of the sampling air a is performed, so an erroneous operation is not performed in the smoke detection.

The embodiments of the present invention are described above. However, the present invention is not limited to the above embodiments. For example, flow configuration of each of the sampling air a and the clean air b is not limited to the columnar or annular shape, and may be an elliptical shape or a rectangular shape. By setting a longitudinal direction thereof along the laser beam L, a light scattering region increases, thereby increasing an amount of the scattered light received by the light receiving element 207. As a result, the fire detection can be performed more quickly and accurately.

The embodiments of the present invention can be implemented by combining requisite portions.

What is claimed is:

1. A smoke detector, comprising:
an optical case having an inner portion constituting a black box;
an air passage which constitutes a smoke detection portion by allowing a gas to flow into the optical case;
a light emitting element disposed in the optical case;
a light receiving element for receiving scattered light generated by scattering light emitted from the light emitting element by smoke particles existing in the smoke detection portion;
a light trap opposed to the light emitting element, for attenuating stray light;
a condenser lens for condensing the light emitted from the light emitting element in the vicinity of the light trap;
a received light amplifier circuit for amplifying an output signal of the light receiving element; and
a fire determination portion for determining fire when a detection level obtained by A/D-converting the amplified output signal is equal to or larger than a threshold value,
wherein the light trap has a curved surface portion having a substantially conical shape and the curved surface portion reflects the stray light a plurality of times and attenuates the stray light, the incident angle θ of the stray light with respect to a tangent line of the curved surface being equal to 45° or less.

2. The smoke detector according to claim 1, wherein the curved surface portion has a coaxial circular shape or an elliptical shape.

3. A smoke detector, comprising:
an optical case including, in a black box:
a light emitting element;
a light receiving element having a predetermined optical axis angle with respect to the light emitting element, for receiving scattered light of the light emitting element scattered by smoke particles in a smoke detection portion; and
an optical trap opposed to the light emitting element, for attenuating stray light; and
an air passage for sampling, which passes across the smoke detection portion of the optical case,
wherein of an inner wall surface in the smoke detection portion of the optical case, a portion in a field range of the light receiving element is formed to be a smooth surface and a portion outside the field range is formed to be an irregular surface.

4. The smoke detector according to claim 3, wherein the smoke detection portion is defined by an aperture for regulating light of the light emitting element.

5. The smoke detector according to claim 4, wherein, when light of the light emitting element passes through the aperture, diffracted light is generated, the diffracted light impinges upon the smooth surface to be reflected outside a field range of a light receiving portion, and the reflected light impinges upon the irregular surface to be attenuated.

6. The smoke detector according to claim 3, wherein, when light of the light emitting element passes through the aperture, diffracted light is generated, the diffracted light impinges upon the smooth surface to be reflected outside a field range of a light receiving portion, and the reflected light impinges upon the irregular surface to be attenuated.

7. A smoke detector, comprising:
an optical case having an inner portion constituting a black box;
a first air passage which constitutes a smoke detection portion by allowing a gas, which is to be detected, to flow into the optical case;
a second air passage arranged in an annular manner surrounding the first air passage for allowing a clean gas to flow through a peripheral portion of the first air passage;
a light emitting element disposed in the optical case;
a light receiving element for receiving scattered light generated by scattering light emitted from the light emitting element by smoke particles existing in the smoke detection portion;
a light trap opposed to the light emitting element, for attenuating stray light;
a received light amplifier circuit for amplifying an output signal of the light receiving element; and
a fire determination portion for determining fire when a detection level obtained by A/D- converting the amplified output signal is equal to or larger than a threshold value.

8. The smoke detector according to claim 7, wherein the fire determination portion comprises control means which adjusts a gas supply amount of one of the first air passage and the second air passage when one of rise in smoke concentration and dirt in the smoke detection portion is detected.

* * * * *